US012770720B2

(12) United States Patent
Bandurski et al.

(10) Patent No.: US 12,770,720 B2
(45) **Date of Patent: *Oct. 20, 2026**

(54) METHOD AND SYSTEM FOR PROVIDING PATIENT DATA TO A PATIENT DATA SERVER FOLLOWING AN OFFLINE NETWORK CONDITION

(71) Applicant: T6 Health Systems LLC, Chestnut Hill, MA (US)

(72) Inventors: Hubert Bandurski, Oakville (CA); Igor Muravyov, Brookline, MA (US); Lewis Cohen, Chestnut Hill, MA (US)

(73) Assignee: T6 Health Systems LLC, Chestnut Hill, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/982,583

(22) Filed: Dec. 16, 2024

(65) Prior Publication Data

US 2025/0191710 A1 Jun. 12, 2025

Related U.S. Application Data

(63) Continuation of application No. 16/387,401, filed on Apr. 17, 2019, now Pat. No. 12,249,408.

(Continued)

(51) Int. Cl.

*G16H 10/60* (2018.01)
*G06F 21/62* (2013.01)

(Continued)

(52) U.S. Cl.

CPC ......... *G16H 10/60* (2018.01); *G06F 21/6218* (2013.01); *G16H 40/63* (2018.01);

(Continued)

(58) Field of Classification Search

CPC ........ G16H 10/60; G16H 40/63; G16H 15/00; G16H 40/20; G06F 21/6218;

(Continued)

(56) References Cited

U.S. PATENT DOCUMENTS

| | | | | |
|---|---|---|---|---|
| 9,934,393 | B2 * | 4/2018 | Johns | G06F 21/6209 |
| 12,249,408 | B2 * | 3/2025 | Bandurski | H04L 9/0894 |

(Continued)

OTHER PUBLICATIONS

One Identity, What is Offline Password Reset option used for and how to set it up?, 2017, https://support.oneidentity.com/password-manager/kb/4219512/what-is-offline-password-reset-option-used-for-and-how-to-set-it-up, https://www.youtube.com/watch?v=YkbOpcV2xk8 (Year: 2017).*

(Continued)

*Primary Examiner* — Kambiz Abdi
*Assistant Examiner* — Tran N Nguyen
(74) *Attorney, Agent, or Firm* — Nutter McClennen & Fish LLP

(57) ABSTRACT

A method and corresponding system for providing patient data to a patient data server following an offline network condition are described. In one arrangement, a healthcare information analysis and presentation system includes a client logic device disposed in wireless communication with a patient data server. The healthcare information analysis and presentation system is configured with an offline functionality that stores patient data on the client logic device, even when not wirelessly connected to the patient data server. Further, the healthcare information analysis and presentation system is configured to allow the end user to begin patient data entry for a new patient, to document an existing case, and to resolve conflicting data following an offline network condition, all while preserving and protecting patient's privacy.

20 Claims, 9 Drawing Sheets

Related U.S. Application Data

(60) Provisional application No. 62/658,890, filed on Apr. 17, 2018.

(51) Int. Cl.

| | |
|---|---|
| ***G16H 40/63*** | (2018.01) |
| ***H04L 9/08*** | (2006.01) |
| *G06F 21/60* | (2013.01) |
| *G16H 15/00* | (2018.01) |
| *H04L 67/12* | (2022.01) |

(52) U.S. Cl.

CPC .......... *H04L 9/0863* (2013.01); *G06F 21/604* (2013.01); *G06F 2221/2141* (2013.01); *G16H 15/00* (2018.01); *H04L 67/12* (2013.01)

(58) Field of Classification Search

CPC ........... G06F 21/604; G06F 2221/2141; G06F 21/6245; H04L 67/12; H04L 2209/88; H04L 67/2861; H04L 69/40; H04L 9/0894

See application file for complete search history.

(56) References Cited

U.S. PATENT DOCUMENTS

| | | | | |
|---|---|---|---|---|
| 2016/0147944 | A1 * | 5/2016 | Douglass ................ | G06F 21/31 705/51 |
| 2020/0244730 | A1 * | 7/2020 | Eteminan ............... | G16H 40/67 |

OTHER PUBLICATIONS

One Identity, What is Offline Password Reset option used for and how to set it up?, 2017, https://support.oneidentity.com/password-manager/kb/4219512/what-is-offline-password-reset-option-used-for-and-how-to-set-it-up, https://www.youtube.com/watch?v=YkbOpcV2xk8 (Year: 2017) (Year: 2017).*

Canadian Office Action for Application No. 3,097,613 dated May 27, 2026 (11 pages).

* cited by examiner

METHOD AND SYSTEM FOR PROVIDING PATIENT DATA TO A PATIENT DATA SERVER FOLLOWING AN OFFLINE NETWORK CONDITION

CROSS-REFERENCE TO RELATED APPLICATION(S)

The present application is a continuation of U.S. patent application Ser. No. 16/387,401 entitled METHOD AND SYSTEM FOR PROVIDING PATIENT DATA TO A PATIENT DATA SERVER FOLLOWING AN OFFLINE NETWORK CONDITION filed Apr. 17, 2019, which claims the benefit of and priority to U.S. Provisional Patent Application No. 62/658,890 filed on Apr. 17, 2018, the entire teachings of each of which is incorporated herein by reference.

BACKGROUND

Advances in policies, assessment, and assurance aspects of injury prevention, pre-hospital care, acute care, and rehabilitation services have been driven by the systematic collection and analysis of patient data, such as in mandated trauma registries. As front line providers of clinical care, medical professionals resuscitating trauma patients and patients with similarly emergent medical conditions (stroke, cardiac arrest, acute care surgery, sepsis, etc.) have ready access to, and a profound understanding of, such patient data. As such, trauma care professionals have a substantial role in the interpretation of these data to policy makers, the design and advocacy of injury and acute medical conditions control strategies, and the ultimate development of injury and acute medical condition control policy.

In certain cases, patient data generated at the point-of-care can be collected by server logic devices within a healthcare information system and used to inform complex decision-making or to improve health system performance. For example, in some healthcare information systems, a healthcare professional can enter patient data into the system using a mobile computerized device, such as a tablet device. The patient data can be entered at the point-of-care, for example, in an ambulance transporting the patient to a healthcare facility, in the emergency department of a hospital, or within a patient examination room of a private medical practice. The patient data can then be transmitted to, and available through, server logic devices of the healthcare information system in real-time or substantially real-time after being entered.

SUMMARY

The flow of patient data among devices within a healthcare information system may be adversely affected due to interruption in connectivity, e.g., wireless connectivity, among the devices. For example, in certain cases, a mobile computerized device may not be able to communicate with server logic devices at various stages of the patient data entry process, e.g., due to an interruption in wireless connectivity between the mobile computerized device and the server logic devices. Alternately, the wireless connection can become slow and unusable. In either case, the inoperability of the wireless connection can limit or prevent transmission of patient data from the mobile computerized device to the server logic devices.

By contrast to conventional healthcare information systems, some embodiments disclosed herein relate to a method and system for providing patient data to a patient data server following an offline network condition. In one aspect, a healthcare information system includes a client logic device in wireless communication with a patient data server. The client logic device is configured with an offline functionality that allows securely storing patient data on the client logic device, even when not wirelessly connected to the patient data server, and transmitting the stored patient data to the server when the wireless connection is reestablished. Further, the healthcare information system is configured to allow the end user to begin patient data entry for a new patient, to document an existing case, and to resolve conflicting data following an offline network condition, all while preserving and protecting patient's privacy.

In one aspect, in order to protect the privacy of a patient's data, the client logic device is configured with an offline user-generated passcode identifier, or PIN code, for each user accessing the patient data server. For example, the user-generated passcode identifier can be stored on the client logic device and tied to a username. The client logic device is further configured to encrypt and store the patient data in a local database. Even after logging out or restarting the device, data remains securely stored by the client logic device. To further protect the patient data, the client logic device is further configured to de-identify the 18 specific identifiers specified by HIPAA.

In a related aspect, in a client logic device, a method for processing patient data is disclosed, which comprises detecting an offline network condition between the client logic device and a patient data server, and in response to the detection of the offline network condition, causing the client logic device to prompt a user to provide the client logic device with a user-generated passcode identifier, where the user-generated passcode identifier is configured to secure patient data stored in the client logic device. The method further includes de-identifying protected health information (PHI), if any, associated with patient data stored in the client logic device, and in response to detecting an online network condition between the client logic device and the patient data server, forwarding patient data associated with at least one patient and a previously assigned medical record number associated with that patient to the patient data server via a network connection.

In some embodiments, in response to detecting the offline network condition between the client logic device and the patient data server, a time interval associated with the offline network condition is checked, and a prompt is initiated to the user after expiration of the time interval. In some embodiments, the method can further include generating, by the patient data server, a communication session between the patient data server and an electronic health record (EHR) system of a medical facility to synchronize the received patient data between the patient data server and the EHR system. The synchronization of the patient data can include utilizing the medical record number to identify the patient associated with the patient data.

The medical record number can be received by the client logic device prior to the detection of the offline network condition. By way of example, the medical record number can be received by establishing, via the patient data server, a communication session between the patient data server and the EHR system and receiving the medical record number from the EHR system.

The medical record number can be received by the client logic device prior to the detection of the offline network condition. By way of example, the medical record number can be received by establishing, via the patient data server, a communication session between the patient data server and the EHR system and receiving, e.g., via a user interface of the client logic device, the medical record number from the patient data server.

In a related aspect, in a client device, a method for processing patient data is disclosed, which includes detecting an offline network condition between the client logic device and a patient data server, and in response to the detection of the offline network condition, causing the client logic device to prompt a user to provide a user-generated access identifier to limit access to the logic device. The method further includes storing patient data on the client logic device via a user interface thereof, where the patient data includes a medical record number and de-identifying protected health information (PHI), if any, associated with the patient data stored on the client logic device to generate de-identified patient data.

In some embodiments of the above method, in response to detecting the offline network condition between the client logic device and a patient data server, a time interval associated with the offline network condition is checked, and a prompt is initiated to a user after expiration of the time interval. Upon detecting, via the client logic device, an online network condition between the client logic device and the patient data server, the de-identified patient data, including the medical record number, which is stored on the client logic device is forwarded, via the network, to the patient data server. Further, the method can include generating a communication session between the patient data server and an electronic health record (EHR) system of a medical facility to synchronize the patient data between the patient data server and the EHR system.

In a related aspect, a method of processing patient data is disclosed, which comprises receiving via at least two client logic devices patient data corresponding to a common patient, said patient data comprising a medical record number, and detecting an offline network condition between at least one of the client logic devices (herein “first logic device”) and a patient data server while at least another one of the client logic devices (herein “second logic device”) continues to be in an online network condition relative to the patient data server and forwarding said patient data to the patient data server. The method further includes causing the first logic device to prompt a user to provide a user-generated access identifier so as to limit access to said first logic device, thereby securing patient data stored on said first logic device, and de-identifying protected health information (PHI), in any, associated with patient data stored on the first logic device. Once an online network connection is detected between the first logic device and the patient data server, the de-identified patient data, including the patient’s medical record, can be forwarded from the first client logic device to the patient data server. Any conflicts between the de-identified patient data sent to the patient data server by the first client logic device and the patient data sent to the patient data server by the second client logic device can be resolved based on a time stamp associated with at least one patient data segment so as to generate consolidated patient data on said patient data server. In some embodiments, a communication session is generated between the patient data server and electronic health record (EHR) system of a medical facility to synchronize the consolidated patient data stored on the patient data server and corresponding patient data stored on the EHR system.

In a related aspect, in a patient data server, a method for synchronizing patient data with a patient database is disclosed, which includes detecting an online network condition between a client logic device and the patient data server, where the online network condition follows an offline network condition. The server receives from the client logic device patient data including a medical record number that identifies a patient associated with the patient data. The method further includes identifying patient data, if any, previously stored on the patient data server associated with the received medical record number and updating the previous patient data based on the received patient data. The updating of the patient data can be achieved, for example, based on a timestamp.

In a related aspect, a method of accessing a client logic device is disclosed, which includes sending from a patient data server encrypted information associated with a user, including a security token, to a client logic device in communication with the patient data server when the user logs into said patient data server, detecting an offline network condition between the client logic device and the patient data server, and decrypting said encrypted information residing on said client logic device to determine whether to provide access to a user attempting to access said client logic device. In some embodiments, the information associated with the user is encrypted using the user’s password as a key.

Further understanding of various aspects of the invention can be obtained by reference to the following detailed description in conjunction with the associated drawings, which are described briefly below.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Embodiments disclosed herein generally relate to a method and system for providing patient data to a patient data server following an offline network condition. In one arrangement, a healthcare information system includes a client logic device in wireless communication with a patient data server. The client logic device is configured with an offline functionality that stores patient data, even when not wirelessly connected to the patient data server. Further, the healthcare information system is configured to allow the end user to begin patient data entry for a new patient, to document an existing case, and to resolve conflicting data following an offline network condition, all while preserving and protecting patient's privacy.

Figure 1:
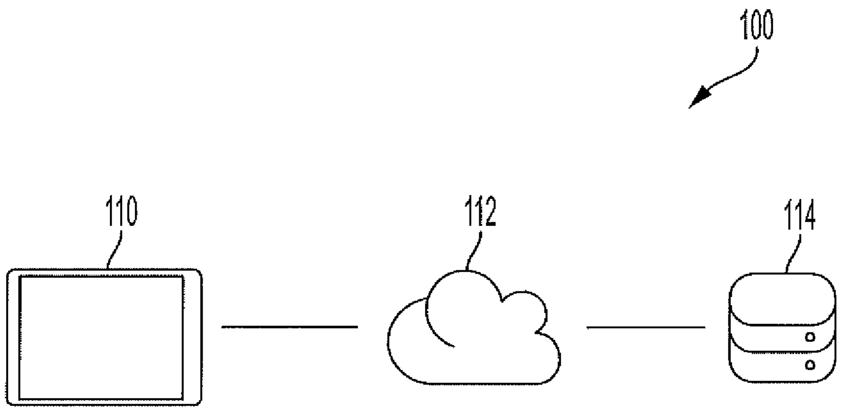
FIG. 1 illustrates a schematic representation of a healthcare information system, according to some embodiments disclosed herein.

FIG. 1 is a schematic representation of a healthcare information system 100, according to one arrangement. The system 100 can be configured as a mobile-device based platform designed for use by front line clinicians for the collection of data when providing healthcare services to patients, such as trauma assessment and resuscitation. In the example illustrated, the system 100 includes one or more client logic devices 110 disposed in electrical communication with an electronic health record (EHR) system 114 of a medical facility via one or more patient data servers 112.

Figure 2:
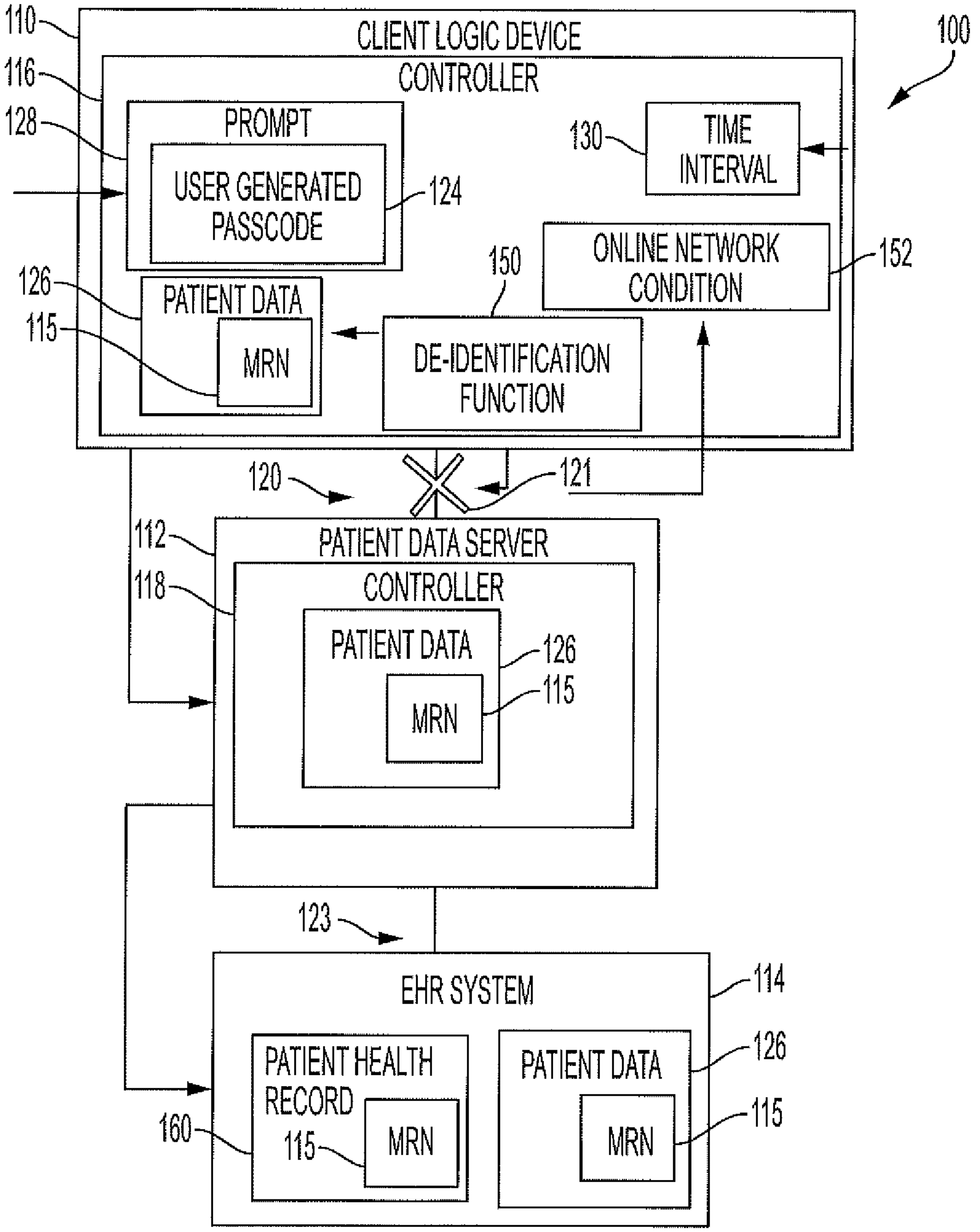
FIG. 2 illustrates a schematic representation of a healthcare information system, according to some embodiments disclosed herein.

With additional reference to FIG. 2, each client logic device 110 is configured as a computerized device having a controller 116, such as a memory and processor. For example, each client logic device 110 can be configured as a mobile computing device, such as a laptop computer, smartphone, personal digital assistant (PDA), tablet computing device, mobile medical equipment, wearable measurement device, or any other mobile computing device. Each client logic device 110 can be configured to communicate with the patient data server 112 via a wireless connection 120 using various communication and data transfer protocols, such as for example, Bluetooth, hypertext transfer protocol (HTTP), Ethernet, WiFi, Health Level 7 International (HL7), cellular communication protocols (e.g., 3G, 4G, LTE, etc.), AirPlay, device-to-device, TCP/IP, API, or any other suitable protocol.

In one arrangement, the client logic device 110 is configured to allow a healthcare professional to enter patient data 126 into the system 100 using a healthcare information application. For example, the controller 116 can be configured to execute a healthcare information application which causes the controller 116 to receive patient data, such as external data, external information, user input, and/or device input, for instance, through the processor and to store the patient data in memory. The patient data 126 can be entered via the client logic device 110 at the point-of-care, for example, in an ambulance transporting the patient to a healthcare facility, in the emergency department of a hospital, or within a patient examination room of a private medical practice.

Patient data server 112 can be configured to control communication and data flow between the client logic devices 110 and the EHR system 114 via a communication connection 123. For example, the patient data server 112 is configured as a computerized device having a controller 118, such as a processor and memory. The memory can include a non-transitory memory or other storage device for storing programming instructions, data, or information regarding one or more applications. During operation, as the patient data server 112 receives patient data 126 from the client logic device 110, the data server 112 can store and/or analyze the received patient data. The patient data server 112 can also communicate with the EHR system 114, e.g., to provide the patient data 126 to the EHR system 114 and/or receive information about the patient from the EHR system 114. By way of example, based on the analysis of the patient data 126, the patient data server 112 can provide an ongoing assessment of the quality and value of healthcare provided to the patient. Further, the patient data server 112 can be configured to provide the patient data 126, as received from the client logic devices 110, to the EHR system 114.

In one implementation, the EHR system 114 can include one or more data stores that are accessible by the client logic devices 110 and/or the patient data server 112. The data stores (not shown) can include patient data such as healthcare information, healthcare assessment processes, historical information, and/or the like. Non-limiting examples of data stores can include healthcare information and management systems (HIMS), electronic medical record (EMR) systems, radiology information systems (RIS), picture archiving and communications system (PACS), medical registries, the National Trauma Data Bank (NTDB) (United States), the National Trauma Registry (NTR) (Canada), medical information repositories, or the like.

The EHR system 114 can make patient data 126 available to end users through the client logic devices 110 in real-time or substantially real time after being entered into the system 100. For example, patient data server 112 can analyze patient data 126 entered by a first medical professional using a first client logic device 110 and generate a medical diagnosis and a treatment assessment that is stored in by the EHR system 114 within the system 100. A second medical professional may access the patient data 126, medical diagnosis, and/or treatment assessment using a second client logic device 110 in real-time or substantially real time after the patient data has been entered into the system 100 by the first medical professional.

In some embodiments, each client logic device 110 is configured to function in the absence of a wireless connection, or during an offline network condition, between the client logic device 110 and the patient server device 112. For example, when an offline network condition occurs between the client logic device 110 and the patient server device 112, the client logic device 110 can securely store patient data, such as either data for a new patient or for an existing patient, while preserving and protecting a patient's privacy. The following provides examples of several types of offline/online scenarios that can occur within the system 100.

Loading an Existing Patient

In some embodiments, the client logic device 110 is configured to allow a user to enter patient data 126 for an existing patient while preserving and protecting patient's privacy.

Figure 3:
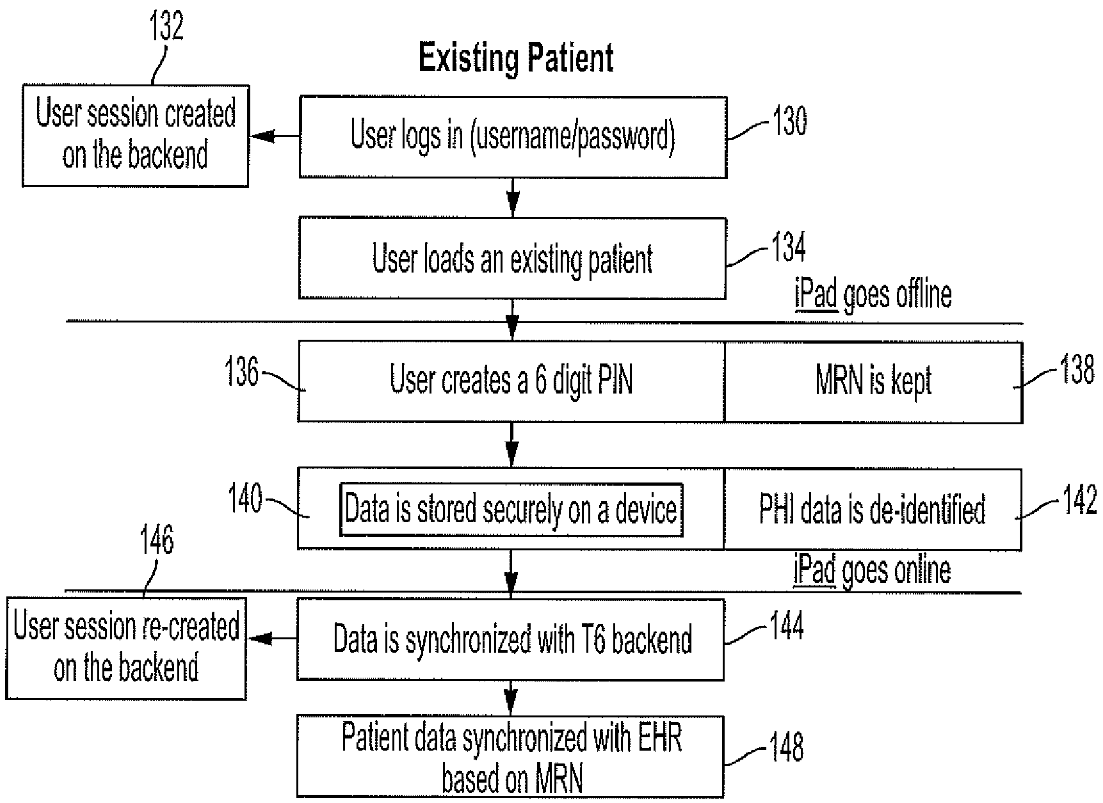
FIG. 3 illustrates an example workflow of the healthcare information system of FIG. 2, according to some embodiments disclosed herein.

For example, with reference to FIGS. 2 and 3, there can be situations where, during an intake procedure, a patient health record 160 for a patient has been created within the EHR system 114 and assigned a corresponding medical record number (MRN) 115. Additionally or alternatively there can be a case where, following the intake procedure, a healthcare professional is examining a patient and wishes to load data generated through the examination of the patient to a client logic device 110 and/or communicate with the EHR system 114, e.g., to retrieve patient data, such as MRN, from the EHR system or transfer patient data to the EHR system. In this case, the user logs into the patient server device 112 through the client logic device 110 using a username and password, as indicated in block 130 of FIG. 3. In response to the patient server device 112 confirming the username and password, the patient server device 112 establishes a data session with the client logic device 110, as indicated in block 132. With the data session established, the user can transmit patient data from the client logic device 110 to the patient server device 112. The user can also retrieve from the EHR system 114 a patient health record 160 associated with the patient, as indicated in block 134 of FIG. 2, based upon the patient's medical record number (MRN) 115 into the client logic device 110.

The client logic device 110 can be configured to receive the MRN 115 in a variety of ways. For example, while an online network condition exists between the client logic device 110 and the patient server device 112, the client logic device 110 is configured to receive the MRN 115 from the patient data server 112 based upon an established communication session between the patient data server 112 and the EHR system 114, such as via network connection 123. In another example, the client logic device 110 can be configured to receive the MRN 115 via a user interface of said client logic device 110. For example, the user or healthcare professional can enter the MRN 115 into the client logic device 110 via a touchscreen or other data entry mechanism. As such, the client logic device 110 can retrieve the patient's health record 160 based upon the patient's MRN 115 and can associate patient data 126 entered into the client logic device 110 with that particular patient based upon the stored MRN 115.

Following the establishment of a wireless network connection 120 between the client logic device 110 and the patient data server 112, a drop or disconnect can occur in the wireless connection 120 between the client logic device 110 and the patient server device 112, resulting in an offline network condition. As a result, the client logic device 110 will not have access to the patient data server 112 and the EHR system 114. However, in such a case, the client logic device 110 is configured to allow the healthcare professional to enter and securely store patient data 126 into the client logic device 110.

For example, in the case where the wireless connection 120 between the client logic device 110 and the patient data server 112 becomes inoperative, the client logic device 110 can detect an offline network condition 121 with the patient data server 112. In one arrangement, during operation, the client logic device 110 is configured to exchange communication with the patient data server 112, such as by sending patient data 126 to the patient data server 112 and receiving acknowledgement of receipt of the patient data. For example, the client logic device 110 can detect an offline network condition when the client logic device 110 fails to receive a response or acknowledgement from the patient data server 112 in response to transmission of a message from the client logic device 110 to the patient data server 112.

In response to detecting the offline network condition 121, the client logic device 110 is configured to prompt a user to create a user-generated passcode identifier 124, such as via prompt 128. In some embodiments, the user can enter a username 130 and can create the user-generated passcode identifier 124, such as a six-digit personal identification number (PIN), as indicated in block 136 of FIG. 3. The client logic device 110 is configured to retain the MRN 115 associated with the patient's health record 160, as indicated in block 138 of FIG. 3, and can continue to receive and store patient data 126 (e.g., medical condition, assessment, etc.), as indicated in block 140 of FIG. 3.

With reference to FIG. 2, while the client logic device 110 can display the prompt 128 at any time, in one arrangement, the client logic device 110 displays the prompt 128 after expiration of a time interval 130 following the detection of the offline network condition 121. For example, in response to detecting the offline network condition 121, the client logic device 110 is configured to check the time interval 130, such as associated with the offline network condition 121, and initiate the prompt 128 after expiration of the time interval 130. In one implementation, during operation, the time interval 130 can be equal to a time of 500 milliseconds. In the event that the client logic device 110 detects an offline network condition 121 relative to the patient data server 112 for 500 milliseconds, the client logic device 110 is configured to provide the prompt 128 to the user to allow the creation of the user-generated passcode identifier 124. The use of a predefined delay between the detection of an offline network condition and the presentation of the prompt 128 to a user advantageously eliminates unnecessary disruption of the use of the client logic device by a medical professional.

As the user enters the patient data 126 into the client logic device 110, the user-generated passcode identifier 124 can allow the client logic device 110 to store the patient data 126 in a secure manner, as indicated in block 140 of FIG. 3.

For example, the user-generated passcode identifier 124 can limit or prevent unauthorized access to the patient data 126. In cases in which the user enters patient data 126 into the client logic device 110 and refrains from interacting with the client logic device 110 for a time period following the patient data entry, the client logic device 110 can enter a sleep mode to conserve power. When a user, either the original user or another user, reengages the client logic device 110, the client logic device 110 is configured to present the user with a prompt requesting a passcode identifier. In the event that the user cannot provide the correct user-generated passcode identifier 124, the client logic device 110 can deny access to the stored patient data 126. However, when the user enters a passcode identifier which matches the user-generated passcode identifier 124, the client logic device 110 can provide access to the patient data 126 stored by the client logic device 110.

In another embodiment, when a user (e.g., a medical professional) logs into the patient data server via a client logic device (e.g., an ipad), the server sends a response containing the first name, the last name, permissions, and a security token, among other information associated with the user. In some embodiments, this information is sent in an encrypted form, e.g., using aes-256, with user's password as a key. This encrypted information persists on the client logic device. When the client logic device is an off-line condition, i.e., in absence of a connection between the client logic device and the patient data server, this information is decrypted and if the decryption is successful, the user is allowed to log into the client logic device to use the device in an offline condition in a manner described herein.

Further, to store the patient data 126 in a secure manner, the client logic device 110 is configured to de-identify protected health information (PHI), if any, associated with patient data 126, as indicated in block 142 of FIG. 3. For example, during a de-identification process, the client logic device 110 is configured to apply a de-identification function 150 to the patient data 126 to strip the patient data 126 of any of eighteen (18) identifiers provided by the HIPAA Privacy Rule. These identifiers include names, geographic data, dates, telephone numbers, FAX numbers, email addresses, Social Security numbers, medical record numbers, health plan beneficiary numbers, account numbers, certificate or license numbers, vehicle identifiers, device identifiers, web URLs, Internet protocol addresses, biometric identifiers, facial images, or unique identifiers or codes.

In response to detecting a transition from an offline network condition to an online network condition 152 with the patient data server 112, the client logic device 110 can be configured to forward the patient data 126 associated with the patient, along with the previously assigned MRN 115 associated with that patient, to the patient data server 112 via a network connection 120.

For example, following the detection of an offline network condition 121, the client logic device 110 can be configured to transmit periodic test communications to the patient data server 112 to determine if the wireless connection 120 has become operative. In the event that the client logic device 110 detects the patient data server 112 has received a test communication, such as by an acknowledgement, the client logic device 110 and the patient data server 112 can identify the wireless connection 120 as having entered an online network condition 152. In such a case, the client logic device 110 is configured to transmit the patient data 126, including the MRN 115, to the patient data server 112. The patient data server 112 can utilize the MRN 115 to update the previously-received data for the patient with the newly-received data. The patient data server 112, can also synchronize the patient data 126 with the EHR system 114, as indicated in block 144 of FIG. 3.

In some embodiments, the patient data server 112 can recreate the user session, as initially established with the client logic device 110, with the EHR system 114, as indicated in block 146 of FIG. 3. For example, the patient data server 112 can generate a communication session between the patient data server 112 and the EHR system 114 to exchange patient data 126 for a patient whose patient health record 160 had been previously retrieved. Next, the patient data server 112 is configured to synchronize, or update, the patient health record 160 stored by the EHR system 114 with the patient data 126 entered at the client logic device 110 based upon the MRN 115, as indicated in block 148 of FIG. 3. For example, the patient data server 112 is configured to transmit the patient data 126 and associated MRN 115 to the EHR system 114. The EHR system 114, in turn, compares the MRN 115 of the patient data 126 with the MRN 115 of each patient health record 160 stored by the EHR system 114. The EHR system 114 utilizes the MRN 115 to identify the patient and patient health record 160 associated with the patient data 126. When the EHR system 114 detects a match in the MRNs 115, the EHR system 114 can update the corresponding patient health record 160 with the patient data 126.

Creating a New Patient

In one arrangement, in the absence of a network connection between the client logic device 110 and the patient data server the client logic device 110 is configured to create a new patient and store patient data 126 related to that patient while preserving and protecting the patient's privacy.

Figure 4:
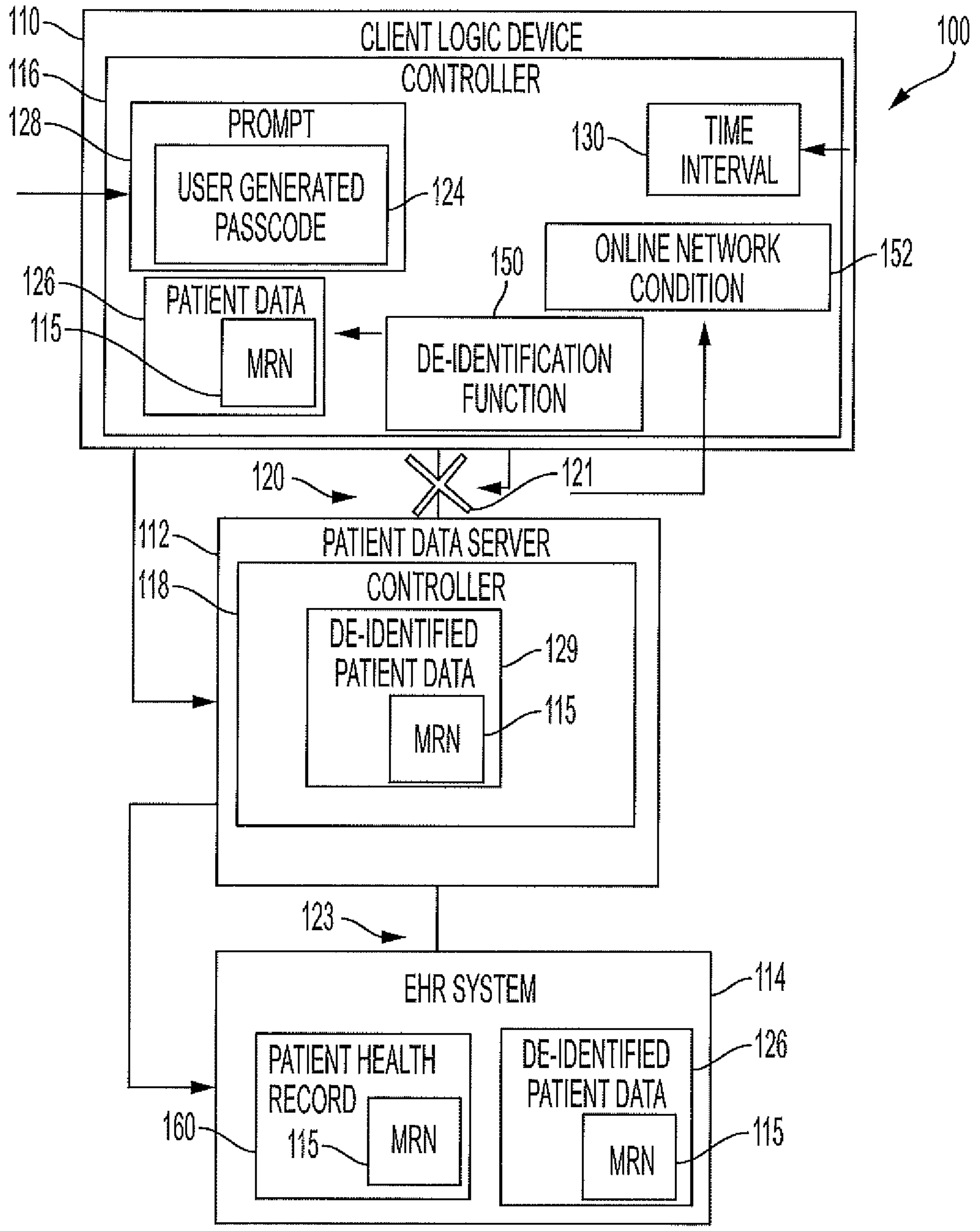
FIG. 4 illustrates a schematic representation of a healthcare information system, according to some embodiments disclosed herein.
Figure 5:
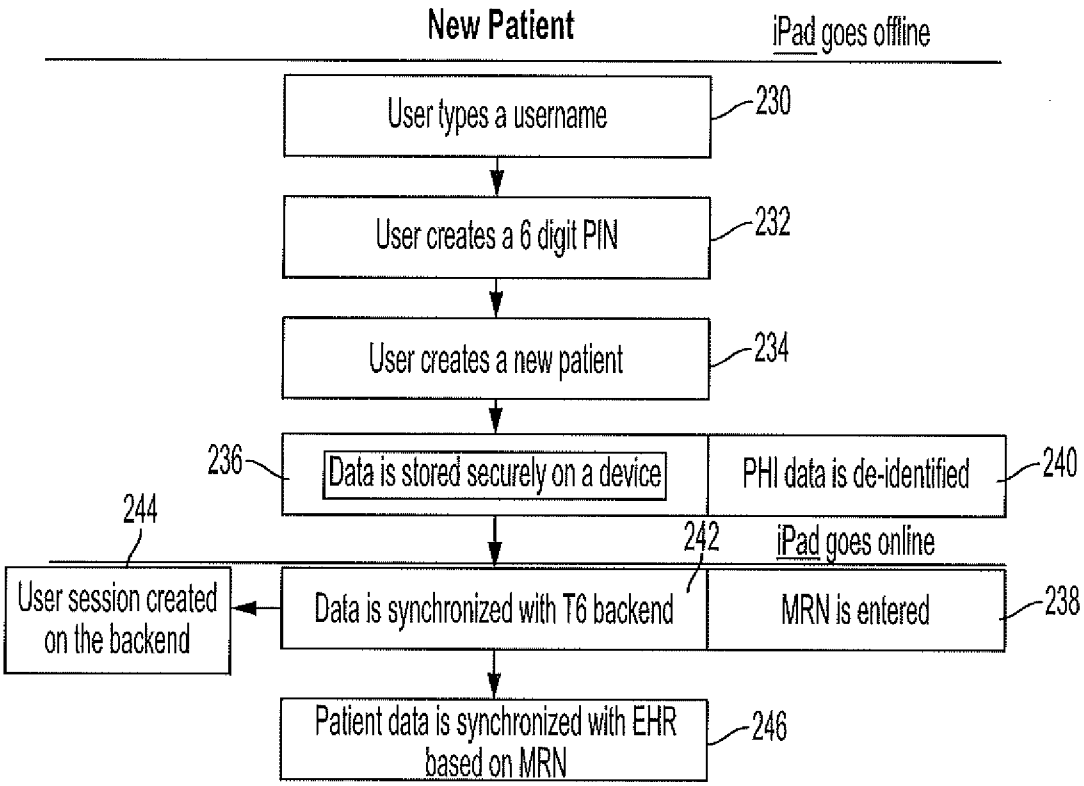
FIG. 5 illustrates an example workflow of the healthcare information system of FIG. 4, according to some embodiments disclosed herein.

For example, with reference to FIGS. 4 and 5, there can be cases where, during an intake procedure, patient profile has been created within the EHR system 114 and assigned a MRN 115. Further, there can be cases where, following the intake procedure, a healthcare professional is examining the patient and wishes to enter patient information, such as patient data 126, to a client logic device 110. However, in this case, prior to entry of patient data into the client logic device 110, a drop or offline network condition can occur in the wireless connection 120 between the client logic device 110 and the patient server device 112 such that the client logic device 110 has not received and does not have access to the patient health record 160 within the EHR system 114. However, in such a case, the client logic device 110 is configured to allow the healthcare professional to enter and securely store patient data 126 into the client logic device 110.

In the case where the wireless connection 120 between the client logic device 110 and a patient server device 112 becomes inoperative, the client logic device 110 is configured to detect an offline network condition 121 between the client logic device 110 and the patient data server 112. For example, during operation, the client logic device 110 is configured to exchange communication with the patient data server 112, such as by sending patient data 126 to the patient data server 112 and receiving acknowledgement of receipt of the patient data. In the event that the client logic device 110 fails to receive a response or acknowledgement from the patient data server 112, the client logic device 110 can identify the wireless connection 120 as having gone offline (i.e., the presence of an offline network condition).

In response to detecting the offline network condition 121, the client logic device 110 is configured to prompt the user to provide a user-generated access identifier 124 to limit access to the client logic device 110. For example, the user can enter a username, as indicated in block 230 of FIG. 5, and can create a six-digit personal identification number (PIN) as the user-generated passcode identifier 124, as indicated in block 232 of FIG. 5. Next, the user can create a new patient with the client logic device 110, such as by entering patient data 126 (e.g., name, birthdate, medical condition, etc.), as indicated in block 234 of FIG. 5.

With reference to FIG. 4, while the client logic device 110 can display the prompt 128 at any time, in one arrangement, the client logic device 110 displays the prompt 128 after expiration of a time interval 130 following the detection of the offline network condition 121 between the client logic device 110 and the patient data server 112. In one arrangement, in response to detecting the offline network condition 121, the client logic device 110 is configured to check a time interval 130 associated with the offline network condition 121 and initiate the prompt 128 after expiration of the time interval 130. For example, the time interval 130 can be equal to a time of 500 milliseconds. In the event that the client logic device 110 remains in an offline network condition 121 relative to the patient data server 112 for the 500 millisecond duration, the client logic device 110 is configured to provide the prompt 128 to the user to allow the creation of the user-generated passcode identifier 124.

Following creation of the user-generated passcode identifier 124, the client logic device 110 is configured to store patient data 126, as indicated in block 236 of FIG. 5, and an MRN 115, as indicated in block 238 of FIG. 5, input via a user interface. For example, the user or healthcare professional can enter a MRN 115 associated with the patient, as well as additional patient data 126 into the client logic device 110 via a touchscreen or other data entry mechanism.

Further, it is noted that as the user enters the patient data 126 into the client logic device 110, the user-generated passcode identifier 124 allows the client logic device 110 to store the patient data 126 in a secure manner 136.

For example, the user-generated passcode identifier 124 can limit or prevent unauthorized access to the patient data 126. Further, there can be cases where the user enters patient data 126 into the client logic device 110 and refrains from interacting with the client logic device 110 for a time period following the patient data entry. In such a case, the client logic device 110 can enter a sleep mode to conserve power. When a user reengages with the client logic device 110, the client logic device 110 can present the user with a prompt which requests the user's previously-generated user-generated passcode identifier 124. In the event that the user cannot provide the correct user-generated passcode identifier 124, the client logic device 110 can maintain itself in an inaccessible or locked state to limit or prevent user access to the stored patient data 126.

Further, to store the patient data 126 in a secure manner when the network connection is in an offline state, the client logic device 110 is configured to de-identify protected health information (PHI), if any, associated with patient data 126, as indicated in block 240 of FIG. 5. For example, during a de-identification process, the client logic device 110 is configured to apply a de-identification function 150 to the patient data 126 to strip the patient data 126 of eighteen (18) identifiers provided by the HIPAA Privacy Rule.

Next, in response to detecting an online network condition 152 with the patient data server 112, the client logic device 110 is configured to forward the patient data 126 associated with the patient, along with the entered MRN 115 associated with that patient, to the patient data server 112 via a network connection 120.

For example, following the detection of an offline network condition 121, the client logic device 110 can be configured to transmit periodic test communications to the patient data server 112 to determine if the wireless connection 120 has become operative. In the event that the client logic device 110 detects the patient data server 112 has received a test communication, such as by an acknowledgement, the client logic device 110 and the patient data server 112 can identify the wireless connection 120 as having entered an online network condition 152. In such a case, the client logic device 110 is configured to transmit the patient data 126, including the MRN 115, to the patient data server 112. The patient data server 112, in turn, can synchronize the patient data 126 with the EHR system 114, as indicated in block 242 of FIG. 5.

During the synchronization process, in one arrangement, the patient data server 112 can create a user session with the EHR system 114, as indicated in block 244 of FIG. 5. For example, the patient data server 112 can generate a communication session between the patient data server 112 and the EHR system 114 to exchange patient data 126 for a patient whose MRN 115 had been entered into the client logic device 110.

Also during the synchronization process, the patient data server 112 is configured to update the patient health record 160 stored by the EHR system 114 with the de-identified patient data 129 provided by the client logic device 110 based upon the MRN 115, as indicated in block 246 of FIG. 5. For example, the patient data server 112 can be configured to transmit the de-identified patient data 129 and associated MRN 115 to the EHR system 114. The EHR system 114 can, in turn, identify the patient based on the MRN 115. This information can be transmitted to patient data server 112 to allow the server to generate a new patient profile and associate the patient data received from the client logic device 110 with that patient. The patient data server 112 can also transmit the patient data received from the client logic device 110 to the EHR system 114 and the EHR system 114 can update the corresponding patient health record 160 with the de-identified patient data 129.

Two Devices Editing the Same Patient Health Record

The healthcare information system 100 allows multiple client logic devices 110 to access and edit a patient health record 169 of the same patient. While this can lead to conflicts in the patient data 126 received by the EHR system 114, in one arrangement, the client logic device 110 is configured to resolve conflicting data.

Figure 6:
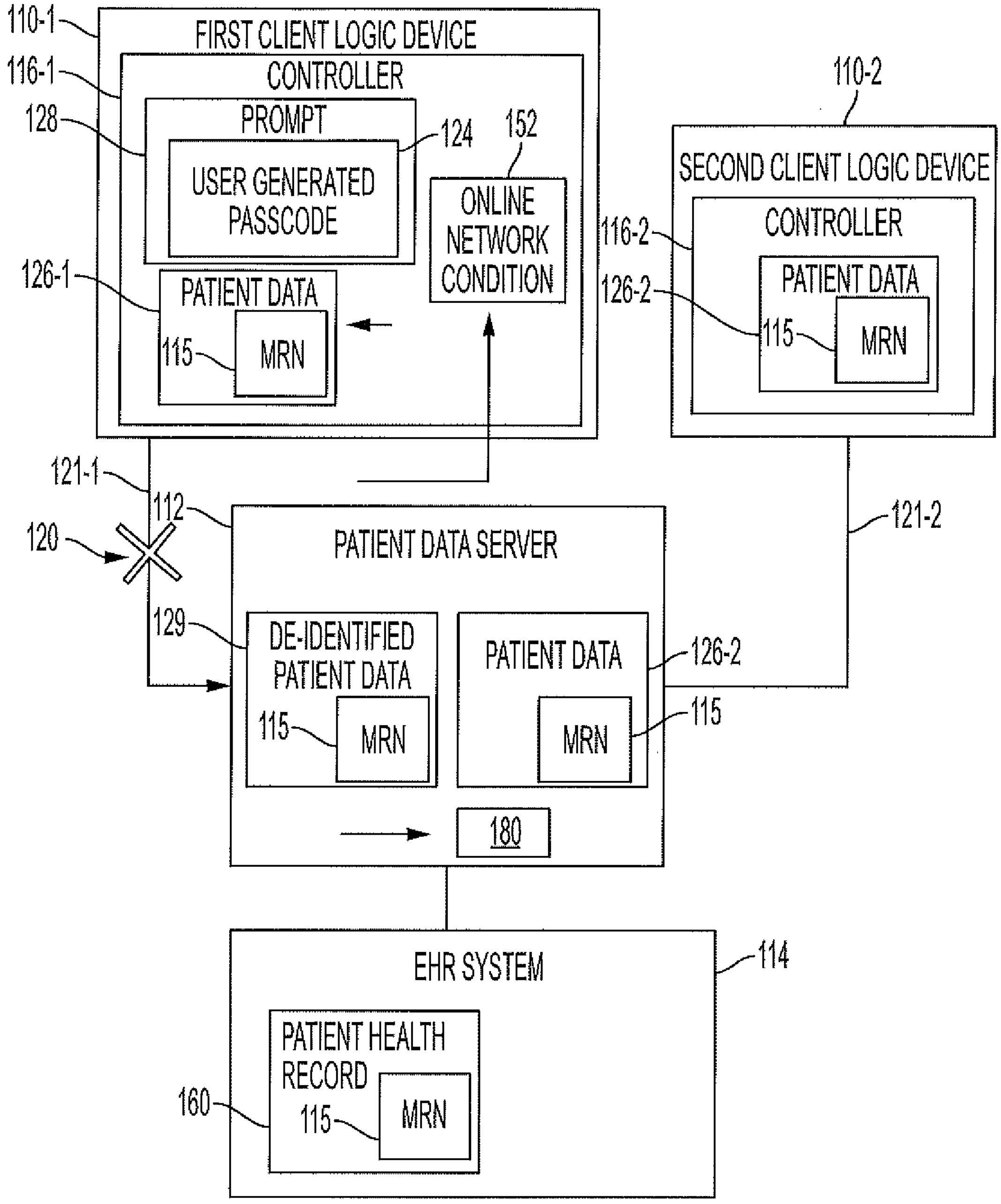
FIG. 6 illustrates a schematic representation of a healthcare information system, according to some embodiments disclosed herein.
Figure 7:
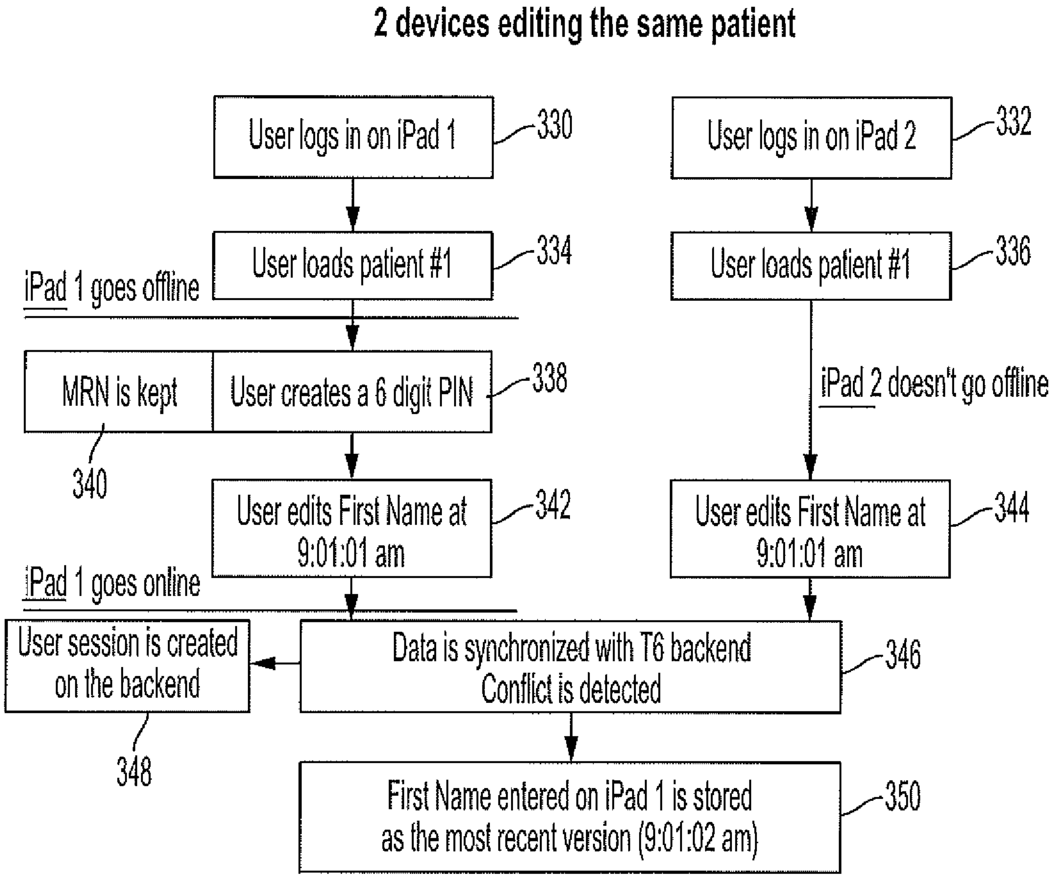
FIG. 7 illustrates an example workflow of the healthcare information system of FIG. 6, according to some embodiments disclosed herein.

For example, with reference to FIGS. 6 and 7, during an intake procedure, an entry (e.g., patient health record 160) fora patient can be created within the EHR system 114 and assigned a corresponding medical record number (MRN) 115. Further, following the intake procedure, a first healthcare professional can decide to provide additional information, such as patient data 126-1, to the EHR system 114 through a first client logic device 110-1 and a second healthcare professional wishes to provide additional information, such as patient data 126-2, to the EHR system 114 through a second client logic device 110-2. In this case, each user logs into the patient server device 112 through their respective client logic device 110-1, 110-2 using a username and password, as indicated in blocks 330 and 332 of FIG. 7. In response to the patient server device 112 confirming the usernames and passwords, the patient server device 112 establishes data sessions with the EHR system 114 for each client logic device 110-1, 110-2. With the data session established, each client logic device 110-1, 110-2 can retrieve the patient health record 160 associated with the common patient, as indicated in blocks 334 and 336 of FIG. 7, based upon the patient's MRN 115.

In some embodiments, following the retrieval of the patient's health record 160, a drop or disconnect can occur in the first wireless connection 120-1 between the first client logic device 110-1 and the patient server device 112. Further, the second wireless connection 120-2 between the second client logic device 110-2 and the patient server device 112 can remain in an online network condition. Here, the first client logic device 110-1 does not have access to the patient's health record 160 within the EHR system 114 and cannot provide additional patient data 126-1 to the EHR system 114 while the second client logic device 110-2 can forward patient data 126-2 to the EHR system 114 via the patient data server 112.

In response to detecting the offline network condition 121, the first client logic device 110-1 is configured to prompt a user to create a user-generated passcode identifier 124, such as via prompt 128. In one arrangement, the user can enter a username 130 and can create the user-generated passcode identifier 124, such as a six-digit personal identification number (PIN), as indicated in block 338 of FIG. 7. The first client logic device 110-1 is configured to retain the MRN 115 associated with the patient's health record 160, as indicated in block 340 of FIG. 7, and can continue to enter and store patient data 126-1 relative to the patient's health record 160 in a secure manner, as indicated in block 342 of FIG. 7. Further, to store the patient data 126 in a secure manner, the first client logic device 110-1 is configured to de-identify protected health information (PHI), if any, associated with patient data 126, as described above.

Next, in response to detecting an online network condition 152 with the patient data server 112, the first client logic device 110-1 is configured to forward the de-identified patient data 129 associated with the patient, along with the previously assigned MRN 115 associated with that patient, to the patient data server 112 via the network connection 120. Further, during the timeframe when first client logic device 110-1 is offline, the second client logic device 110-2 can continue to receive and store patient data 126-2 relative to the patient's health record 160 in a secure manner, as indicated in block 344 of FIG. 7, and can forward the patient data 126-2 to the patient data server 112. Accordingly, the patient data server 112 allows more than one user to access the patient health record 160 and can receive patient data 129, 126-2 from the devices 110-1, 110-2 at substantially the same time. However, conflicts may arise in the sets of patient data 129, 126-2 received from the devices 110-1, 110-2. As such, the patient data server 112 is configured to resolve conflicts occurring between patient data 129, 126-2 from the devices 110-1, 110-2, so as to generate consolidated patient data 180.

In one arrangement, the patient data server 112 is configured to resolve conflicts occurring between patient data 129, 126-2 based upon a time stamp associated with patient data 129, 126-2. For example, block 342 of FIG. 7 indicates that the first client logic device 110-1 updated the First Name of the patient data 129 at 9:01:02 am (offline) while block 344 indicates that the second client logic device 110-2 updated the First Name of the patient data 126-2 at 9:01:01 am (online). When the first client logic device 110-1 comes online, the patient data server 112 can identify the First Name of the patient data 129, as stored on the first client logic device 110-1 as the most recent version. Accordingly, in this conflict regarding the First Name, the patient data server 112 can utilize the First Name of the patient data 129, as stored on the first client logic device 110-1, as part of the consolidated patient data 180.

Following consolidation of the patient data, the patient data server 112 is configured to establish a communication session with the EHR system 114 (FIG. 7, block 346) to synchronize the consolidated patient data stored 180 with the patient data (e.g., patient health record 160) stored on the EHR system 114 (FIG. 7, block 348). For example, the patient data server 112 can identify a patient health record 160 previously stored on the EHR system 114 based upon an associated MRN 115. In the event that the patient data server 112 identifies such a patient health record 160, the patient data server 112 is configured to update the patient health record 160 with the consolidated patient data 180 (i.e., using the First Name of the patient data 129, as stored on the first client logic device 110-1, as part of the consolidated patient data 180; FIG. 7, block 250).

Loading Offline Stored Patient

In some embodiments, the client logic device 110 is configured to allow the user to access and edit existing patient data 126 stored by the client logic device 110. An example of the workflow of the healthcare information system 100 in such a case is provided in FIG. 8.

Figure 8:
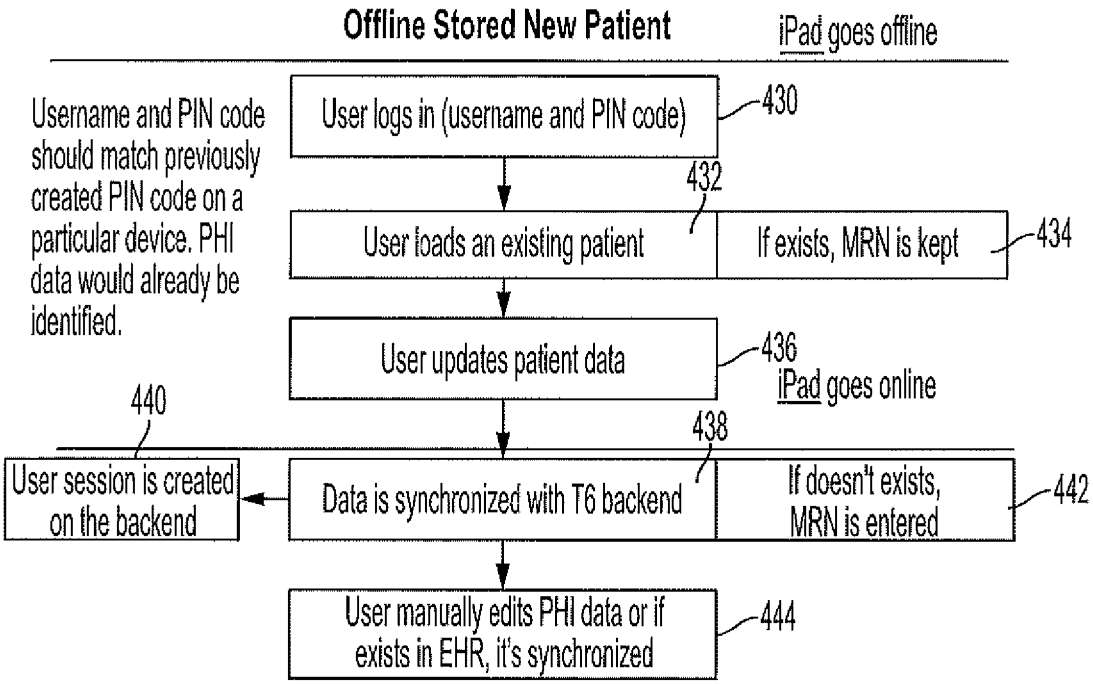
FIG. 8 illustrates an example workflow of a healthcare information system, according to some embodiments disclosed herein, and FIG. 9 schematically illustrates an example of implementation of any of a client logic device and/or a patient data server according to an embodiment of the present teachings.

In some embodiments, an offline network condition can exist between the client logic device 110 and the patient data server 112. In embodiments in which a user has previously stored patient data 126 with the client logic device 110 and refrains from interacting with the client logic device 110 for a time period following the patient data entry. In such a case, the client logic device 110 can enter a sleep mode to conserve power. When a user, either the original user or another user, engages the client logic device 110, the client logic device 110 is configured to present the user with a prompt which requests a passcode identifier. In the event that the user enters a passcode identifier which matches the user-generated passcode identifier 124 (FIG. 8, block 430), the client logic device 110 can provide access to the patient data 126 stored by the client logic device 110 (FIG. 8, block 432). If the stored patient data 126 includes a previously-entered MRN 115, the client logic device 110 retains the MRN 115 with the patient data 126 (FIG. 8, block 434) and the user can update the patient data 126 FIG. 8, block 436).

Next, in response to detecting an online network condition with the patient data server 112, the client logic device 110 is configured to forward the patient data 126 associated with the patient, along with the entered MRN 115 associated with that patient, to the patient data server 112 via a network connection 120. The patient data server 112, in turn, can synchronize the patient data 126 with the EHR system 114 (FIG. 8, block 438).

During the synchronization process, in one arrangement, the patient data server 112 can create a user session with the EHR system 114 (FIG. 8, block 440). For example, the patient data server 112 can generate a communication session between the patient data server 112 and the EHR system 114 to exchange patient data 126 for a patient whose MRN 115 had been entered into the client logic device 110. Alternately, if the patient data 126 does not include an associated MRN 115, the user can enter the MRN 115 (FIG. 8, block 442), such as via the client logic device 110.

Also during the synchronization process, the patient data server 112 is configured to update the patient health record 160 stored by the EHR system 114 with the patient data 126, if de-identified, provided by the client logic device 110 based upon the MRN 115 (FIG. 8, block 444). Alternately, the PHI of the patient data 126 can be manually de-identified and synchronized with the patient health record 160.

As provided above, the system 100 includes one or more client logic devices 110 disposed in electrical communication with an electronic health record (EHR) system 114 (e.g., EPIC) of a medical facility via one or more patient data servers 112 (e.g., a T6 platform). Such description is by way of example only. In one arrangement, the system 100 includes one or more client logic devices 110 disposed in electrical communication with one or more additional patient servers via the patient data servers 112.

Further, it is noted that in some embodiments the flow of the operations shown and described above can be performed in a mutually exclusive manner. For example, as provided above, the client logic device 110 can be configured to de-identify protected health information (PHI), if any, associated with patient data 126. However, upon de-identification of the PHI data, a user may have to re-enter the data manually if the PHI data is not present in an associated EHR system 114.

Figure 9:
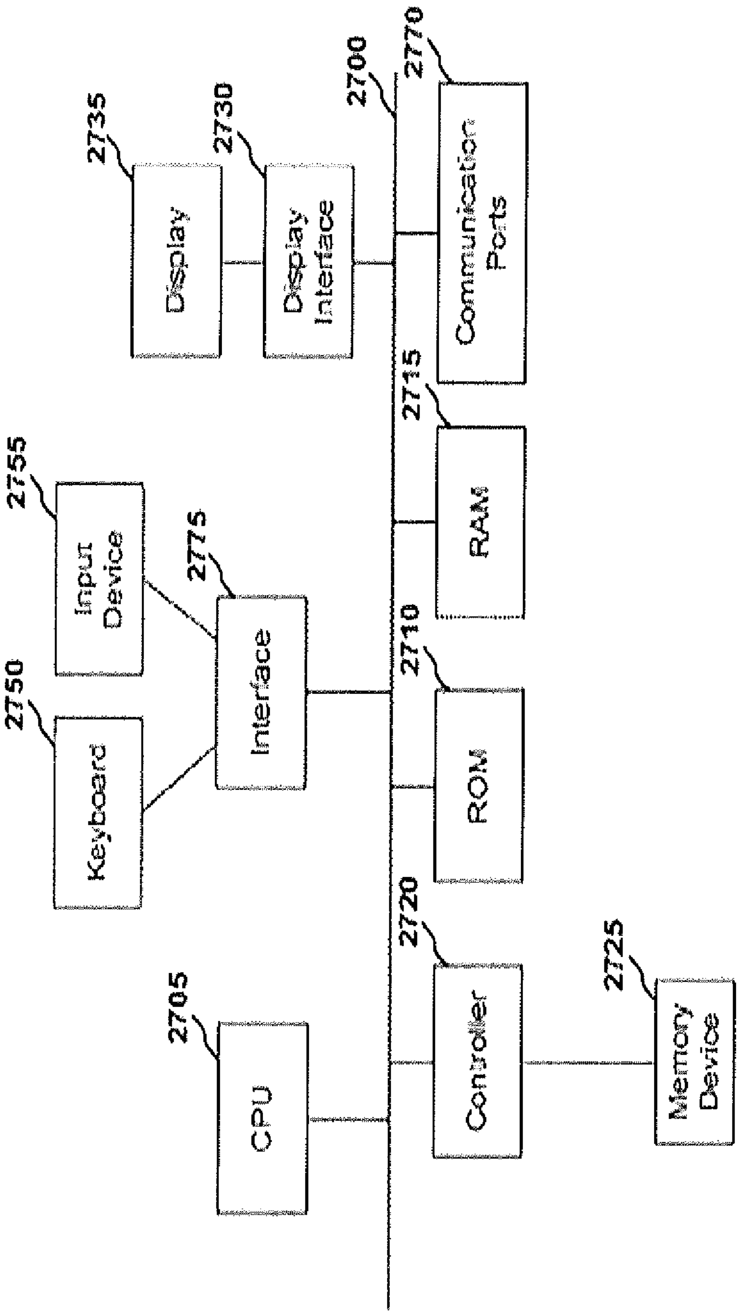

A client logic device and/or a patient data server according to the present teachings can be implemented in hardware, firmware and software using known techniques informed by the present teachings. By way of example, FIG. 9 depicts a block diagram of exemplary internal hardware that may be used to contain or implement the various computer processes and systems as discussed above. A bus 2700 serves as the main information highway interconnecting the other illustrated components of the hardware. CPU 2705 is the central processing unit of the system, performing calculations and logic operations required to execute a program. CPU 2705 is an exemplary processing device, computing device or processor as such terms are used within this disclosure. Read only memory (ROM) 2730 and random access memory (RAM) 2735 constitute exemplary memory devices.

A controller 2720 interfaces with one or more optional memory devices 2725 to the system bus 2700. These memory devices 2725 may include, for example, an external or internal DVD drive, a CD ROM drive, a hard drive, flash memory, a USB drive or the like. As indicated previously, these various drives and controllers are optional devices. Additionally, the memory devices 2725 may be configured to include individual files for storing any software modules or instructions, auxiliary data, common files for storing groups of results or auxiliary, or one or more databases for storing the result information, auxiliary data, and related information as discussed above. For example, the memory devices 2725 may be configured to store healthcare information 325, healthcare analysis processes 330 and/or data contained in the data stores 115.

Program instructions, software or interactive modules for performing any of the functional steps associated with the analysis and presentation of healthcare information as described above may be stored in the ROM (read only memory) 2730 and/or the RAM (random access memory) 2735. Optionally, the program instructions may be stored on a tangible computer-readable medium such as a compact disk, a digital disk, flash memory, a memory card, a USB drive, an optical disc storage medium, such as a Blu-Ray™ disc, and/or other recording medium.

An optional display interface 2730 may permit information from the bus 2700 to be displayed on the display 2735 in audio, visual, graphic or alphanumeric format. The information may include information related to a current job ticket and associated tasks. Communication with external devices may occur using various communication ports 2740. An exemplary communication port 2740 may be attached to a communications network, such as the Internet or a local area network.

The hardware may also include an interface 2745 which allows for receipt of data from input devices such as a keyboard 2750 or other input device 2755 such as a mouse, a joystick, a touch screen, a remote control, a pointing device, a video input device and/or an audio input device.

Computer program logic implementing all or part of the functionality previously described herein may be embodied in various forms, including, but in no way limited to, a source code form, a computer executable form, and various intermediate forms (for example, forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in a non-transitory form (for example, a source code form, a computer executable form, an intermediate form, or combinations thereof) in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

By way of example, the present teachings can be implemented in a healthcare information analysis and graphical display presentation system disclosed in U.S. Publication No. 2016/0019352A1, which is herein incorporated by reference in its entirety.

While various embodiments have been particularly shown and described, it will be understood by those skilled in the art that various changes in form and details may be made therein without departing from the spirit and scope of the invention as defined by the appended claims.

What is claimed is:

1. A system for processing patient data, the system comprising:
- a client logic device including at least one processor configured to perform processes comprising:
- establishing a communication connection between the client logic device and a patient data server;
- detecting that the communication connection has become inoperative to form an offline network condition between the client logic device and the patient data server;
- in response to the detection of the offline network condition, causing the client logic device to prompt a user to create at the client logic device a user-generated passcode identifier for use during the offline network condition to limit or prevent unauthorized access to patient data stored in the client logic device, wherein the patient data is associated with a previously assigned medical record number;
- storing the user-generated passcode identifier on the client logic device;
- receiving offline patient data from the user;
- applying a de-identification function to the offline patient data to strip the patient data of any protected health information (PHI) other than the previously assigned medical record number;
- encrypting and storing the offline patient data in a local database;
- upon detecting that the user has refrained from interacting with the client logic device for a predetermined amount of time, placing the client logic device in a sleep mode;
- upon detecting reengagement with the client logic device after placing the client logic device in the sleep mode, causing the client logic device to present a prompt requesting entry of the user-generated passcode identifier;
- upon detecting entry of an incorrect user-generated passcode identifier in response to the prompt requesting entry of the user-generated passcode identifier, denying access to the stored de-identified patient data;
- upon detecting entry of the correct user-generated passcode identifier in response to the prompt requesting entry of the user-generated passcode identifier, providing access to the stored de-identified patient data; and
- in response to detecting transition from the offline network condition to an online network condition between the client logic device and the patient data server, forwarding the de-identified patient data and the previously assigned medical record number to the patient data server via the communication connection.

2. The system of claim 1, wherein, in response to detecting the offline network condition between the client logic device and the patient data server, the at least one processor is configured to perform further processes comprising:

checking a time interval associated with the offline network condition; and initiating a prompt to a user after expiration of the time interval.

3. The system of claim 1, further comprising:

the patient data server, wherein the patient data server is configured to generate a communication session between the patient data server and an electronic health record (EHR) system of a medical facility to synchronize the received patient data between the patient data server and the EHR system.

4. The system of claim 3, wherein synchronizing the patient data comprises utilizing the medical record number to identify the patient associated with the patient data.

5. The system of claim 3, wherein the at least one processor is configured to receive the medical record number prior to detecting the offline network condition.

6. The system of claim 1, wherein the at least one processor is configured to receive the medical record number from the patient data server.

7. The system of claim 1, wherein the at least one processor is configured to receive the medical record number via a user interface of the client logic device.

8. A system for processing patient data, the system comprising:

a client logic device including at least one processor configured to perform processes comprising:

establishing a communication connection between the client logic device and a patient data server;

detecting that the communication connection has become inoperative to form an offline network condition between the client logic device and the patient data server;

in response to the detection of the offline network condition, causing the client logic device to prompt a user to create a user-generated access identifier for use during the offline network condition to limit or prevent unauthorized access to the logic device;

storing the user-generated passcode identifier on the client logic device;

receiving offline patient data via a user interface of the client logic device, the offline patient data comprising a medical record number;

applying a de-identification function to the offline patient data to strip the patient data of any protected health information (PHI) other than the previously assigned medical record number;

encrypting and storing the offline patient data in a local database; and providing access to the client logic device during the offline network condition upon entry of the user-generated passcode identifier at the client logic device.

9. The system of claim 8, wherein, in response to detecting the offline network condition between the client logic device and the patient data server, the at least one processor is configured to perform further processes comprising:

checking a time interval associated with the offline network condition; and initiating a prompt to a user after expiration of the time interval.

10. The system of claim 8, wherein the at least one processor is configured to perform further processes comprising:

detecting via the client logic device an online network condition between the client logic device and the patient data server; and forwarding the de-identified patient data, including the medical record number, stored on the client logic device via the network to the patient data server.

11. The system of claim 10, further comprising:

the patient data server, wherein the patient data server is configured to generate a communication session between the patient data server and an electronic health record (EHR) system of a medical facility to synchronize the patient data between the patient data server and the EHR system.

12. A system for processing patient data, the system comprising:

a patient data server;

a first client logic device in communication with the patient data server; and a second client logic device in communication with the patient data server, wherein:

the patient data server is configured to receive, from the first and second client logic devices, patient data corresponding to a common patient, the patient data comprising a medical record number;

the first client logic device is configured to:

establish a communication connection between the client logic device and the patient data server;

detect that the communication connection has become inoperative to form an offline network condition between the client logic device and the patient data server;

prompt a user to create a user-generated access identifier for use during the offline network condition to limit or prevent unauthorized access to the first client logic device and to store the user-generated access identifier on the first client logic device, thereby securing patient data stored on the first client logic device;

apply a de-identification function to the offline patient data on the first client logic device to strip the patient data of any protected health information (PHI) other than the previously assigned medical record number;

encrypt and store the offline patient data in a local database on the first client logic device;

provide access to the first client logic device during the offline network condition upon entry of the user-generated passcode identifier at the first client logic device;

detect transition from the offline network condition to an online network condition between the first client logic device and the patient data server; and forward the de-identified patient data, including the medical record number, from the first client logic device to the patient data server via the communication connection; and the patient data server is configured to resolve conflicts between the de-identified patient data sent to the patient data server by the first client logic device and patient data sent to the patient data server by the second client logic device during the offline network condition between the first client logic device and the patient data server based on a time stamp associated with at least one patient data segment to generate consolidated patient data on the patient data server.

13. The system of claim 12, wherein the patient data server is configured to generate a communication session between the patient data server and an electronic health record (EHR) system of a medical facility to synchronize the consolidated patient data stored on the patient data server and corresponding patient data stored on the EHR system.

14. The system of claim 12, wherein resolving conflicts comprises:

identifying previous patient data, if any, previously stored on the patient data server associated with the received medical record number; and updating the previous patient data based on the received de-identified patient data.

15. The system of claim 14, wherein updating the previous patient data based on the received patient data comprises updating the previous patient data based on a timestamp.

16. The system of claim 1, wherein the PHI stripped from the patient data includes at least one of names, geographic data, dates, telephone numbers, FAX numbers, email addresses, Social Security numbers, health plan beneficiary numbers, account numbers, certificate or license numbers, vehicle identifiers, device identifiers, web URLs, Internet protocol addresses, biometric identifiers, facial images, or unique identifiers or codes.

17. The system of claim 8, wherein the PHI stripped from the patient data includes at least one of names, geographic data, dates, telephone numbers, FAX numbers, email addresses, Social Security numbers, health plan beneficiary numbers, account numbers, certificate or license numbers, vehicle identifiers, device identifiers, web URLs, Internet protocol addresses, biometric identifiers, facial images, or unique identifiers or codes.

18. The system of claim 12, wherein the PHI stripped from the patient data includes at least one of names, geographic data, dates, telephone numbers, FAX numbers, email addresses, Social Security numbers, health plan beneficiary numbers, account numbers, certificate or license numbers, vehicle identifiers, device identifiers, web URLs, Internet protocol addresses, biometric identifiers, facial images, or unique identifiers or codes.

19. A system for accessing a client logic device, the system comprising:

a client logic device including at least one processor configured to perform processes comprising:

establishing a communication connection between the client logic device and a patient data server;

detecting that the communication connection has become inoperative to form a first offline network condition between the client logic device and the patient data server;

in response to the detection of the first offline network condition, causing the client logic device to prompt a user to create at the client logic device a user-generated passcode identifier for use during offline network conditions to limit or prevent unauthorized access to patient data stored in the client logic device;

storing the user-generated passcode identifier on the client logic device;

receiving encrypted information associated with a user from the patient data server in communication with the client logic device when the user logs into the patient data server from the client logic device;

persisting the encrypted information on the client logic device;

detecting a second offline network condition between the client logic device and the patient data server;

decrypting, after detecting the second offline network condition, the encrypted information residing on the client logic device;

applying a de-identification function to the decrypted information to strip the decrypted information of any protected health information (PHI) other than a previously assigned medical record number;

causing, after decrypting the encrypted information, presentation of a prompt on the client logic device, wherein the prompt is configured to receive additional log in information including the user-generated passcode identifier;

receiving the additional log in information; and providing access to the information on the client logic device upon receiving the additional log in information.

20. The system of claim 19, wherein the user logs into the patient data server through the client logic device using a username and password, and wherein the information associated with the user is encrypted using the user's password as a key.

* * * * *